United States Patent [19]
Kassal et al.

[11] Patent Number: 5,885,222
[45] Date of Patent: Mar. 23, 1999

[54] DISPOSABLE ACOUSTIC PAD SENSORS

[75] Inventors: James Kassal, East Lyme; William Reeves, Branford; A. Christian Hilmer, Essex, all of Conn.

[73] Assignee: MedAcoustics, Inc., Raleigh, N.C.

[21] Appl. No.: 802,593

[22] Filed: Feb. 19, 1997

Related U.S. Application Data

[63] Continuation of Ser. No. 114,198, Aug. 30, 1993, abandoned.

[51] Int. Cl.⁶ .......................................................... A61B 5/02
[52] U.S. Cl. ............................................. 600/528; 128/773
[58] Field of Search ..................... 600/372, 382, 600/586, 528; 128/773

[56] References Cited

U.S. PATENT DOCUMENTS

| | | | |
|---|---|---|---|
| 4,054,808 | 10/1977 | Tanaka | 310/323 |
| 5,035,247 | 7/1991 | Heimann | 128/715 |

FOREIGN PATENT DOCUMENTS

| | | | | |
|---|---|---|---|---|
| 0 201 421 | 11/1986 | European Pat. Off. | .......... | H04R 1/46 |
| 0 528 279 A1 | 2/1993 | European Pat. Off. | ...... | H01L 41/113 |
| 2 507 424 | 12/1982 | France | .............. | H04R 1/46 |
| 32 34 584 A1 | 3/1984 | Germany | .......... | G01D 5/24 |
| WO 94/05207 | 3/1994 | WIPO | .............. | A61B 7/04 |

*Primary Examiner*—Scott M. Getzow
*Attorney, Agent, or Firm*—Myers Bigel Sibley & Sajovec

[57] ABSTRACT

The present invention relates to an acoustic sensor device for capturing internal body sounds. The acoustic sensor device is designed to sense the flexing of a patient's skin that is a result of the localized nature of internal body sounds, especially the patient's heart sounds, and generate an electrical signal analogous to the flexure of the skin. The acoustic sensing device of the present invention has as its principal components two thin film piezoelectric sensing portions, preferably formed from polyvinylidene fluoride or a similar piezoelectric material, two layers of a compliant, substantially incompressible material, a flexible and elastic adhesive layer between respective ones of the sensing portions and the incompressible material layers, an electrical connector at one end of the sensing device, an optional neutral plane inducer, an electrostatic shield for the electrical connector, a moisture barrier/protective coating, and an optional adhesive or cream layer for adhering the sensor device to the skin of the patient.

26 Claims, 3 Drawing Sheets

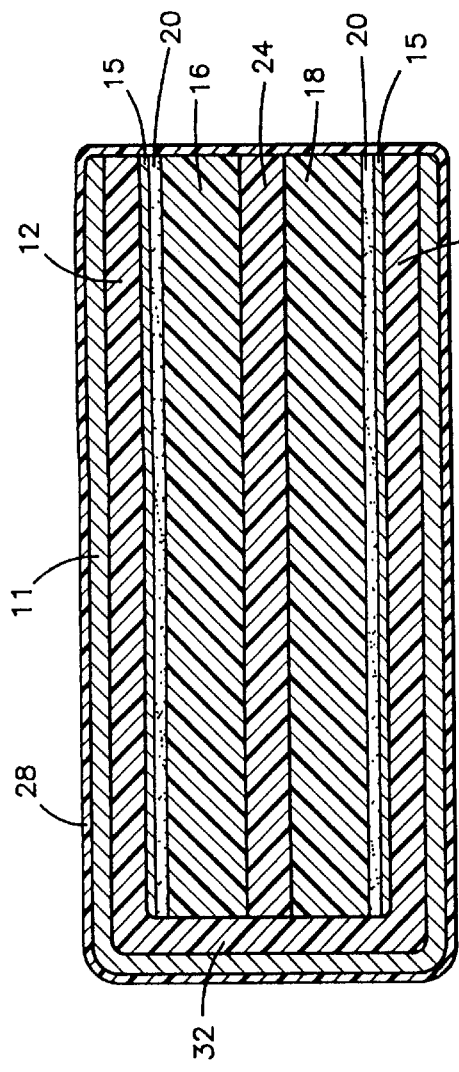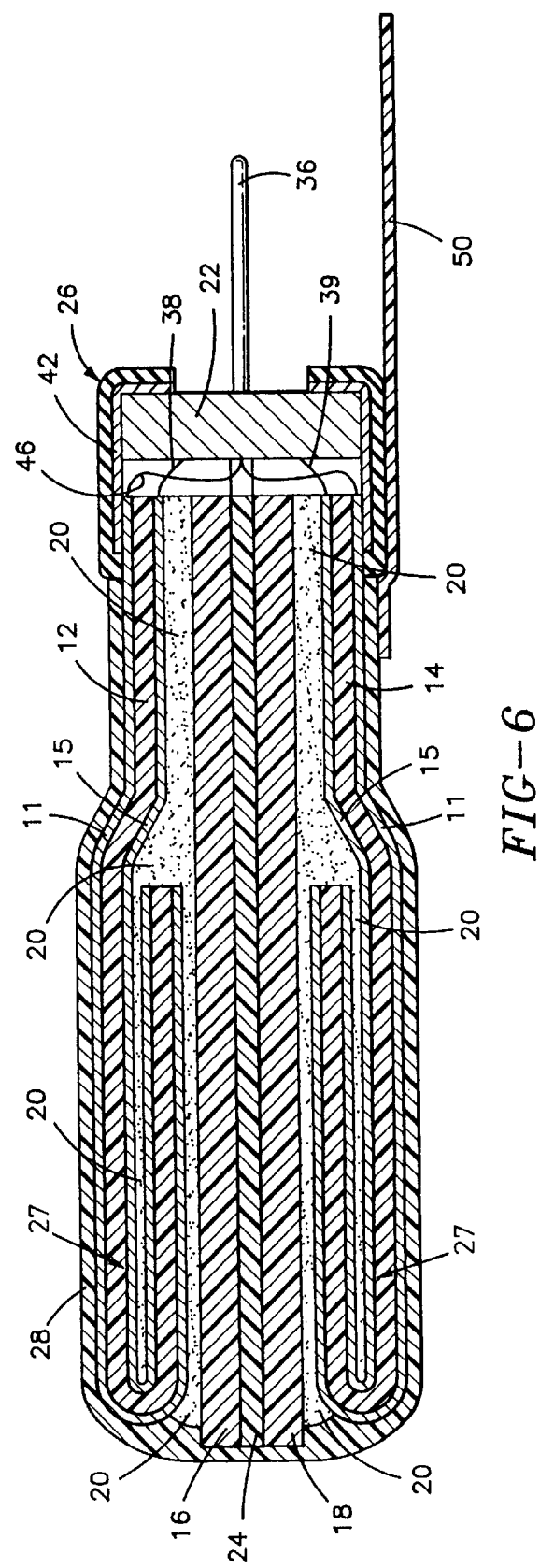

DISPOSABLE ACOUSTIC PAD SENSORS

This is a continuation of 08/114,198, filed Sep. 30, 1993, now abandoned.

BACKGROUND OF THE INVENTION

The present invention relates to disposable acoustic pad sensors for capturing heart sounds which have particular utility in digital acoustic cardiography, phonocardiography and acoustic spectral analysis applications.

Acoustic pick-up devices that have been traditionally used for capturing heart sounds have had two distinct disadvantages: (A) they have a poor signal to noise ratio in that they are very sensitive to air-borne noise which requires that a special, quiet room be used for procedures; and (B) they are fairly massive in size and therefore substantially reduce the surface vibrations they are trying to detect.

Commercially available contact microphones are sometimes used to capture heart sounds because they reduce the pick-up of extraneous sounds. On the negative side however is the fact that they influence the surface vibrations even more than other types of pick-ups.

Many of these devices have an additional disadvantage in that they must be held in place. This can introduce unwanted noise from the unavoidable quivering of muscles and creaking of joints in the user's fingers. Belts could be used to avoid this but many users find them objectionable from a convenience standpoint. Still further, many present sensor devices incur signal losses due to air coupling and non-contaneous conformance with the skin.

The sensor of the present invention described herein substantially avoids all these disadvantages while offering other totally unique and desirable features.

SUMMARY OF THE INVENTION

Accordingly, it is an object of the present invention to provide an acoustic sensor for detecting heart sounds which is easy to use and of very light weight.

It is also an object of the present invention to provide an acoustic sensor as above which is matched to the soft tissue mechanical impedance of the patient's chest to maximize signal output.

It is a further object of the present invention to provide an acoustic sensor as above which is sufficiently low in cost to make it a disposable item and which is also practical for single patient use.

It is yet a further object of the present invention to provide an acoustic sensor as above which can be applied to a patient's skin with adhesive or electrode cream.

The foregoing objects and advantages are attained by the acoustic sensor of the present invention. In accordance therewith, the sensor comprises a pad sensor having a desired surface area which is mechanically and acoustically coupled over substantially all of its surface area to a wall of a patient's chest. The pad sensor senses flexure of the chest wall in response to sound produced by the patient's heart. The pad sensor is designed to have a flexure rigidity, that in conjunction with the mechanical properties of the human tissues forming the chest wall, produces maximum output of the device. Effectively, the chest wall becomes a part of the sensing device.

In a preferred embodiment of the present invention, the pad sensor forming the sensor has two spaced apart piezoelectric sensing portions with metallized inner and outer surfaces. The piezoelectric sensing portions are spaced a distance apart that creates a maximum voltage signal. This spacing is provided by first and second separating layers of a compliant, substantially incompressible material and an optional neutral plane inducer. Preferably, the piezoelectric sensing portions are formed from a piezoelectric material such as polyvinylidene fluoride.

The pad sensor also has an electrical connector along one edge. The connector is electrically connected to the metallized surfaces of the piezoelectric sensing portions. The connector is provided with means for shielding the connector from interfering signals due to extraneous electromagnetic fields.

The sensor further includes a moisture barrier adjacent external surface(s) of the piezoelectric sensing portions. The sensor may also include a layer of adhesive material or cream to mechanically couple the sensor to the patient's chest wall. In a preferred embodiment of the present invention, the layer of adhesive material covers an area larger than the surface area of the external surface closest to the patient's chest wall. The adhesive layer influences flexure rigidity of the chest wall with the pad sensor applied thereto. The overall design of the pad sensor of the present invention accounts for this physical property of the adhesive.

The sensor of the present invention has particular utility in digital acoustic cardiography, phonocardiography, acoustic spectral analysis and other biomedical applications.

Still other objects and advantages to the present invention are set out in the following description and drawings wherein like reference numerals depict like elements.

BRIEF DESCRIPTION OF THE DRAWINGS

FIG. 5 is a sectional view of an alternative embodiment of a sensor which is formed by folding the piezoelectric material about its long axis; and FIG. 6 is a sectional view of yet another embodiment of a sensor in accordance with the present invention.

DETAILED DESCRIPTION OF THE PREFERRED EMBODIMENT(S)

The acoustic sensor device described herein can be termed an acoustic pad because it is a thin, pad-like device. It is intended for single patient use like an ECG electrode patch but in some cases, it may be possible to use the acoustic sensor device of the present invention multiple times before it needs to be discarded. The acoustic sensor device is designed to be compliant and conform to the contour of the chest wall of the patient to which it is attached. Preferably, it is mechanically and acoustically coupled by a substantially void-free adhesive to the chest wall over substantially its entire surface area.

Figure 1:
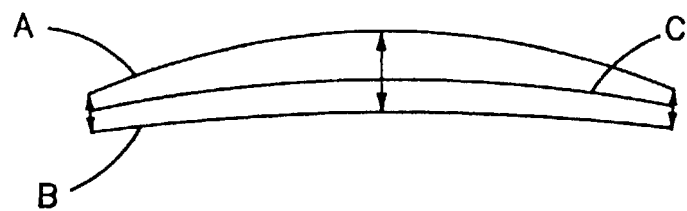
FIG. 1 is an illustration of skin flexure due to localized vibration displacements.

The acoustic sensor device of the present invention is designed to sense the flexing of the chest wall that is a result of the localized nature of the heart sounds. The four primary cardiac auscultation sites used by physicians to evaluate the function of the four heart valves are fairly small in area. At the center of these areas, sound intensity related to valvular function is at a maximum. Two or three centimeters off these centers, the sound intensity is considerably lower. This localized nature is true also for sounds produced by turbulent flow through restrictive sections of arteries, and by respiration. Thus, the amplitude of the vibration of the chest wall is larger at the center of an auscultation area than at its edges. Curves A and B in FIG. 1 represent the extremes of the inward/outward displacement of a line drawn on the skin. The time separating curves A and B is one-half the period of the vibratory motion. The arrows illustrate the amplitude of the vibratory motion at the center and edges of the auscultation site. Curve A is different in contour from curves B and C, thus demonstrating that the skin must be flexing as well as moving perpendicular to its surface. Curve C represents the undisturbed skin contour between heart beats.

The acoustic sensor device 10 of the present invention is designed to flex with the skin. This flexure produces dynamic tensile strain in piezoelectric sensing portions 12 and 14 and thus an electrical signal (voltage) analogous to the flexure is generated by the acoustic sensor device. The flexural rigidity of the acoustic sensor device is designed so that in conjunction with the mechanical flexure impedance of the soft chest tissue, a maximum output signal is produced in response to cardiac sounds. This mechanical impedance matching is an important and totally unique feature of the acoustic sensing device of the present invention.

Figure 2:
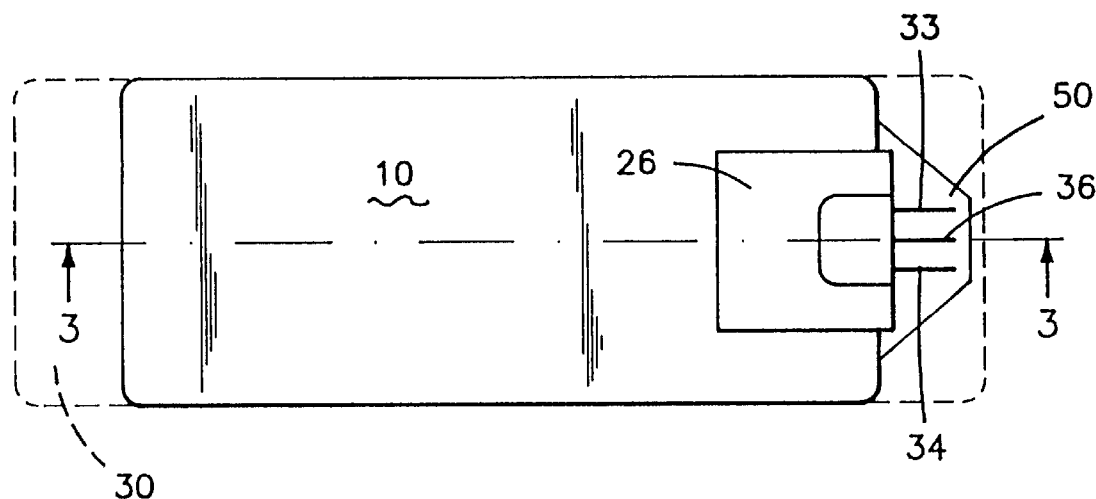
FIG. 2 is a top view of a sensor in accordance with the present invention.
Figure 3:
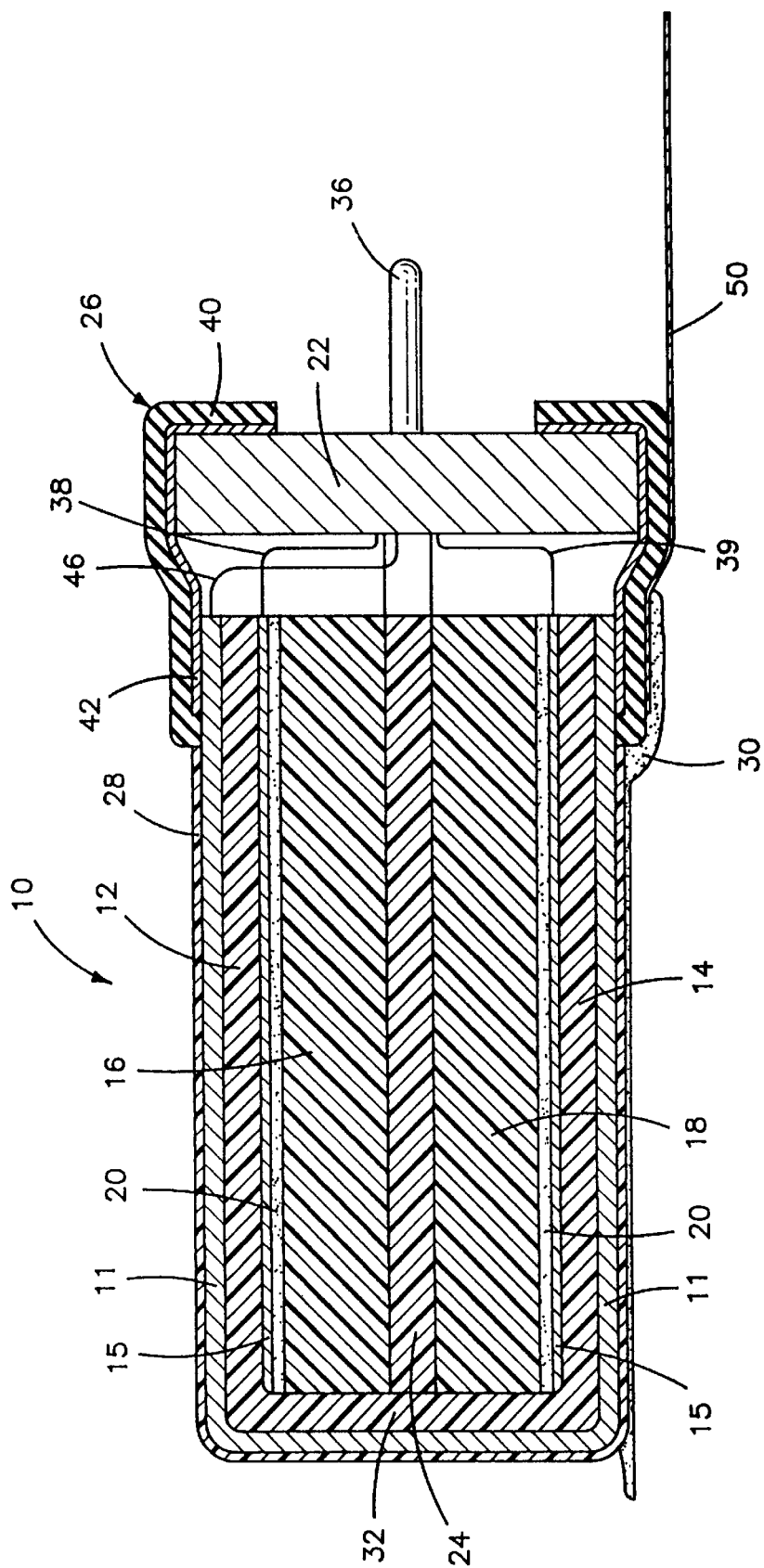
FIG. 3 is a sectional view of the sensor of FIG. 2 taken along lines 3—3.

Referring now to FIGS. 2 and 3, the acoustic sensing device 10 of the present invention has as its principal components: two thin film piezoelectric sensing portions 12 and 14 formed from a piezoelectric material such as polyvinylidene fluoride or a similar piezoelectric co-polymer; two layers 16 and 18 of a compliant, substantially incompressible material; a flexible and elastic adhesive layer 20 between respective ones of the sensing portions 12 and 14 and the layers 16 and 18; an electrical connector 22 along one edge of the sensing device; an optional neutral plane inducer 24; an electrostatic shield 26; a moisture barrier/protective coating 28; and an optional adhesive or cream layer 30 for adhering the sensor device to the patient's skin.

The piezoelectric sensing portions 12 and 14 may be formed by separate pieces of a piezoelectric material having metallized inner and outer layers. Alternatively, as shown in FIGS. 3 and 5, the sensing portions 12 and 14 may be formed by the end portions of a single strip of piezoelectric material having metallized inner and outer surfaces. When the sensing portions are formed from a single strip, an electrical discontinuity is created along the inner surface. In other words, a central portion 32 of the strip material is not metallized along its inner surface.

Metallization of the surfaces of the sensing portions 12 and 14 may be accomplished using any suitable material and any suitable technique known in the art. For example, very thin layers 11 and 15 of a metal, such as nickel, silver, copper or alloys thereof, may be deposited on the inner and outer surfaces of the sensing portions. Alternatively, the surfaces could be coated with a conducting ink. Typically, when a tensile strain is imposed on the piezoelectric material, one metallized surface acquires a positive charge relative to the other. Preferably, in the embodiment of FIG. 3, a continuous metal layer 11 is formed on the outer surface of the piezoelectric material.

The piezoelectric sensing portions 12 and 14 have a thickness which depends on the Young's modulus, dielectric constant, and the separation between the portions 12 and 14. They may each have a thickness of about 52 microns or less, with a preferred thickness being about 28 microns or less. Additionally, they may be configured so that the long dimension of the sensing portions 12 and 14 is parallel to the stretch axis of the piezoelectric material to produce the maximum signal.

Polyvinylidene fluoride (PVDF) has been found to be a useful material for the sensing portions. It is an anisotropic piezoelectric polymer that produces surface charges of equal magnitude and opposite polarity on opposite surfaces when a mechanical strain is imposed on the material. Another material which may be used for the sensing portions is a piezoelectric co-polymer that is 75% vinylidene fluoride by weight.

It has been found that the size of the surface charges Q on the sensing portions 12 and 14 is proportional to the size of the strain. Thus, for a given force applied to the sensing portions 12 and 14 along their length, the size of the strain is inversely proportional to its thickness (all other dimensions and properties being considered constant). The capacitance C between the surfaces is also inversely proportional to the thickness. Because the voltage V across the thickness is given by $V=Q/C$, it is not a function of the thickness of the sensing elements.

Output impedance of the sensor device is inversely proportional to the thickness. As a result, it is advantageous to keep output impedance as low as practical within other physical and operational constraints because it decreases the size of the required input impedance of the amplifier to which it is connected for phonocardiography and acoustic spectral analysis applications. Keeping the impedance low also reduces the vulnerability of the acoustic sensing device and its connecting cable to electromagnetic interference. Thus, very thin, high capacitance sensing portions 12 and 14 are important.

The internal surfaces of the sensing portions 12 and 14 are bonded to the layers 16 and 18 by adhesive layers 20. The adhesive material forming the adhesive layer may comprise any suitable elastic adhesive material known in the art. Generally, the sensing portions 12 and 14 are arranged so that the internal surfaces are the positive surfaces. In this way, the two positive surfaces are electrically isolated from each other by the layers 16 and 18 and by the electrical discontinuity in the central portion 32. However, the internal surfaces could also be negative without altering performance except for a phase shift in the output signal relative to the positive internal configuration.

The layers 16 and 18 are formed from a compliant, substantially incompressible material. Preferably, they are formed from an elastomeric material such as nitrile, neoprene, latex, polyethylene or very dense polyethylene forms. While the layers 16 and 18 are illustrated as having the same thickness, they could have different thicknesses.

The tensile stiffness of the layers 16 and 18 is preferably significantly less than the tensile stiffness of the sensing portions 12 and 14. When the layers 16 and 18 are bonded to the neutral plane inducer 24, the assembly must be flexible, i.e. easily bent around an axis in a plane of a layer 16 and 18 and perpendicular to the symmetry axis that parallels the long dimension of the assembly. The flexural rigidity of an assembly of the layers 16 and 18 (without sensing portions 12 and 14) must be much less than the flexural rigidity which exists in a mode where the sensing portions 12 and 14 are bonded to the outer surfaces of the layers 16 and 18. The thickness of the layers 16 and 18 and thus the separation of the sensing portions 12 and 14 strongly influences the overall flexural rigidity of the device. A total separation of the sensing portions 12 and 14 of about 0.025 inches is desirable for many applications. The ideal separation is that which causes a maximum voltage signal to be developed by the sensing portions 12 and 14 in response to acoustic energy that emanates from heart valves or other sources internal within the body and is incident on the skin area to which the acoustic sensing device is applied. Too much separation between the sensing portions 12 and 14 can cause the acoustic sensing device to be so stiff that flexure of the skin is severely impeded and thus there will be little (dynamic) strain in the sensor portions 12 and 14. Too little separation can allow the acoustic sensing device to be very flexible and move with the skin with virtually no influence on flexure of the skin, but there will be almost no voltage developed in the sensing portions 12 and 14 because the skin does not flex very much (in response to the acoustic heart valve or other signals) even when unimpeded.

An essential part of the sensing device of the present invention is that the sensing portions 12 and 14 are optimally separated to achieve maximum voltage signals in the sensing portions. It should be recognized however that this separation may be different for different patient characteristics and different sources of sound within the body. In other words, the mechanical impedance of the acoustic sensing device is matched to the mechanical impedance of the soft tissue to which it is applied to maximize the electrical output signal. Each sensing portion of the pad preferably has a capacitance as measured at 1000 Hz of between 2.0 and 3.0 nF with a quality (Q) factor of at least 45 to ensure that the device is functioning appropriately.

Figure 4:
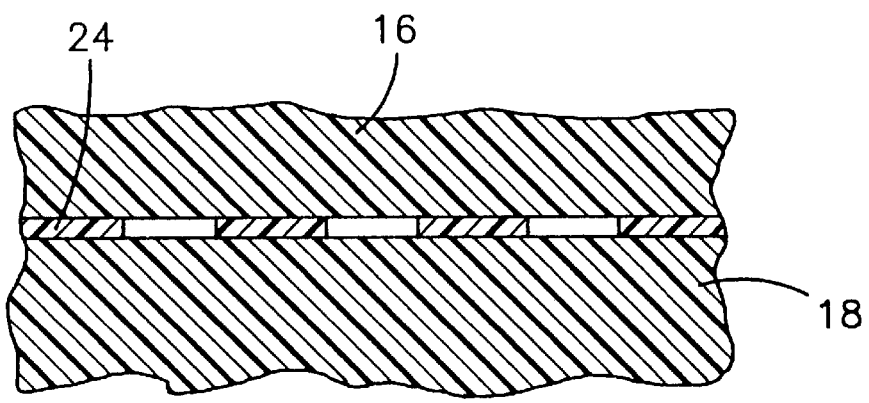
FIG. 4 is a partial sectional view of the sensor of FIG. 2 illustrating an alternate arrangement for the neutral plane inducer.

The optional neutral plane inducer 24 may be formed from a very thin sheet of metal such as copper foil or inelastic plastic such as a 0.5–10.0 mil polyester or acetate sheet bonded to the inner surfaces of the layers 16 and 18. The material from which it is formed should flex but not stretch. If desired, the neutral plane inducer may be split into a series of narrow strips as shown in FIG. 4 that traverse the narrow dimension of the layers 16 and 18 provided that the strips are separated by small, parallel gaps that run perpendicular to the long dimension of the layers 16 and 18. The neutral plane inducer could also be a layer of an adhesive, such as a flexible epoxy adhesive, used to bond the two layers together provided that the flexibility and the tensile stiffness of the cured adhesive are appropriate.

The neutral plane inducer 24 preferably has: (A) a tensile stiffness several times larger, i.e. at least about 3 times larger, than the tensile stiffness of the layers 16 and 18 and the tensile stiffness of the sensing portions 12 and 14; and (B) little resistance to bending about an axis that is perpendicular to the long dimension of the device and in the plane of the device. Its purpose is to force the layers 16 and 18 to have substantially equal tensile and compressive forces when the sensor is bent. For some applications, it may be helpful for the inducer 24 to have a stiffness substantially equal to that of the layers 16 and 18 and/or that of the sensing portions 12 and 14.

If no neutral plane inducer is employed in the sensing device 10, a single double thick pad of material may be used in lieu of layers 16 and 18 to produce the desired separation of the sensing elements 12 and 14.

As previously mentioned, an electrical connector 22 is disposed along one edge of the sensing device. The connector preferably has a three conductor or pin arrangement which includes two outer pins 33 and 34 and a central pin 36. The two outer pins 33 and 34 are electrically connected by conductors 38 and 39 to the metallized inner, positive surface(s) of the sensing portions 12 and 14. The center pin 36 is electrically connected to the external, negative surface (s) of the sensing portions 12 and 14 by conductor(s) 46.

While the connector 22 has been illustrated as spanning the width of the sensor, it may be necessary to position the connector so that the pins 33, 34 and 36 are off the center plane of the device, i.e. on one side of a plane defined by the upper surface of layer 24, in order to accommodate a mating connector without interfering with application of the device to the patient.

In the embodiment shown in FIG. 3, the metallized external surfaces of the sensing portions 12 and 14 are formed by a single continuous metallized surface. When applied to a patient, the electrical signals present at the two outer conductors or pins 33 and 34 are opposite to each other. That is, as the signal of one inner (positive) surface goes positive relative to its outer negative surface, the signal of the other inner positive surface goes negative relative to its outer surface. This is because as the skin and therefore the acoustic sensing device flexes, one sensing portion experiences tensile strain while the other sensing portion experiences compressive strain. Because compressive strains cause charges of opposite polarity from tensile strains, the two voltages are opposite in polarity.

It should be noted that the sensing portions 12 and 14 also respond to pressure applied to the surfaces. In this way, both the signals produced by the sensing portions 12 and 14 are in phase and of equal magnitude. Therefore, they are common mode signals and are not amplified but rather canceled by each other. This means the acoustic sensing device, when coupled with suitable electronics (which do not form part of the present invention), is not sensitive to air-borne acoustic energy except when that energy causes flexure of the sensing device.

A shield 26 is placed over the connector 22 to minimize, to the maximum extent possible, the pick-up of interfering signals caused by extraneous electromagnetic fields. The shield 26 may be effected by coating an inner surface of an insulating layer 40 placed over the connector 22 with a layer 42 of a conducting ink, a conducting paint, or metallic foil such as copper foil that is in electrical contact with the external metallized surface(s) 11 of the sensing portions. Alternatively, shielding may be provided by an outer layer of metallization, i.e. copper, on the sensing portions 12 and 14 or by extending the sensing portions (12 and 14), with metallization (11) on the outside surface only, to cover the connector.

A moisture barrier or protective coating 28 suitable for skin contact is formed about the external surface(s) 11 of the sensing portions. The barrier may be formed from any suitable flexible material known in the art that will keep moisture out of the sensor device 10. It may be a spray-on or dipped coating, a thin film laminate, or non-porous medical grade tape. The moisture layer must be elastic and have only a small effect on the flexibility of the device.

A layer 30 of an adherent material is used to maintain intimate contact between the skin of the patient and the acoustic sensing device so that the acoustic sensing device flexes along with the skin. The layer 30 may be an integral part of the sensing device 10 or may be a separately applied layer which is formed during application of the sensing device to the patient.

The adhesive layer 30 may be in the form of a viscous cream or gel for patients with chest hair to avoid shaving the hair. Alternatively, the layer 30 could be formed by a layer of an adhesive tape or a medical adhesive. While not necessary, it is desirable that a gel or a cream be used even when the layer 30 is formed from an adhesive tape. The adhesive layer 30 acts to mat down chest hair and avoid scraping sounds. It must not substantially alter the combined flexibility of skin and the adhered sensor.

The adherent material layer 30, as shown in FIG. 2, preferably covers an area of the skin greater than the area defined by the lower surface of the sensing device 10. As used herein, the term lower surface refers to the surface of the device 10 closest to the patient's skin.

The adherent material layer 30 may be bonded to the moisture barrier 28 along the surface of the sensor directed towards the chest of the patient using any suitable bonding agent known in the art.

A bib 50 formed from any plastic or similar material suitable for contact with skin is preferably provided to keep the adhesive 30 from contacting the connector pins and the mating cable connector (not shown).

The acoustic sensing device or pad of the present invention may be used with a differential amplifier, one that amplifies the algebraic difference between the voltage levels of the inner surfaces of the sensing portions 12 and 14. Interfering signals on the two signal leads (outer pins 33 and 34) caused by extraneous (and pervasive) electromagnetic fields will be essentially identical in level and in phase because the leads are symmetrically placed and very close to each other. Thus, the interfering signals are not amplified by the differential amplifier and in fact will essentially disappear from the signal of interest in the differential amplifier. As a result, it can be said that the sensing device of the present invention has a balanced output for use with an instrument amplifier. This feature makes the sensing device of the present invention unique among all acoustic pick-ups for digital acoustic cardiography, phonocardiography and other forms of biological acoustic spectral analysis.

As can be seen from the foregoing discussion, the sensing device of the present invention possesses many advantages. For example, it conforms to the contour of the patient and can be applied to the skin of the patient with adhesive or electrode cream and without shaving any body hair. It senses skin flexure in response to cardiac and other internally generated sounds and is used to create analogous electrical'signals. Still further, the sensing device's flexibility is adjusted in accordance with the soft tissue mechanical impedance to maximize signal output. The sensing device is designed for single patient use, can be produced at a relatively low cost, and is very light in weight. Finally, the sensing device provides a balanced electrical output and air-borne sound produces common mode signals that are canceled via active noise cancellation by the electronics to which the acoustic sensing device is designed to be coupled.

The dimensions of the acoustic sensing device will vary depending on the particular characteristics of the intended patient (pediatric, obese, geriatric, etc.). It will in general be rectangular in shape and not larger than about 2.5 in.×about 2.0 in.×about 0.080 in. thick. A typical sensor for adult use would be about 1.1 in.×about 1.5 in.×about 0.050 in. thick with a small electrical connector that increases the thickness to as much as about 0.25 in. over an area of about 0.2 sq. in.

FIG. 5 illustrates an alternative embodiment in which the sensor is formed by folding the single sheet of piezoelectric material forming the sensing portions about its longitudinal axis. A shown, therein the sensor is characterized by sensing portions 12 and 14 formed from a folded sheet of piezoelectric material. As before, the sensor includes layers 16 and 18 of a compliant substantially incompressible material, adhesive layers 20, neutral plane inducer 24, metallization layers 11 and 15, moisture barrier 28 and a central non-metallized portion 32. In such a construction, the electrical connector 22 may be placed along a longitudinal edge of the sensor if desired.

In yet another alternative construction, a sensor may be formed by folding the piezoelectric material film onto itself prior to wrapping the film around the separation layers and the optional neutral plane inducer. This works very well to reduce the physical size of the device provided other physical characteristics are changed. FIG. 6 illustrates a sectional view of such a sensor.

The sensor as shown in FIG. 6 has sensing portions 12 and 14 formed by sheets of piezoelectric material each having a folded over portion 27. The folded over portion 27 for each sheet may extend over the entire length of the sensor. As in the embodiment of FIG. 3, the sensor has layers 16 and 18 of a compliant substantially incompressible material and adhesive layers 20 bonding the folded over regions of the piezoelectric material to each other and bonding the sensing portions 12 and 14 to the layers 16 and 18. Each sheet of piezoelectric material is provided with metallization layers 11 and 15.

The sensor may also include a neutral plane inducer 24 and an electrical connector 22. The connector may have three pins and may be connected to the metallization layers in the manner previously discussed. Preferably, shielding means 26 are provided for the sensor.

Still further, the sensor includes a moisture barrier 28, a layer of adhesive material (not shown) to maintain intimate contact between the patient's skin and the sensor, and a bib 50 to protect the connector 22.

In any of the aforementioned sensor embodiments, the sensor device of the present invention can be made in substantially the same way except that a curvature of radius about 1 to 3 inches is provided to make it easier for the device to conform to body curvature.

While the acoustic sensors of the present invention have particular utility in biomedical applications, they could also be used in mechanical applications such as sensing fluid flow in a pipe.

It is apparent that there has been provided in accordance with this invention disposable acoustic pad sensors which fully satisfy the objects, means and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. An acoustic sensor for capturing sounds produced within a body, the sensor comprising:

a pad having a desired surface area;

said pad being adapted to be mechanically and acoustically coupled over substantially all of said surface area to a portion of a patient's skin;

said pad sensing flexure of said skin in response to sound produced within a patient's body and having a flexure rigidity adjusted to the mechanical impedance of skin tissue;

said pad having a spaced apart first and second piezoelectric portions for sensing said flexure and for converting said sensed flexure into electrical signals; and said first and second piezoelectric sensing portions being spaced apart a distance which creates a maximum voltage signal in said sensing portions.

2. The sensor of claim 1 wherein said first and second sensing portions are formed from a material selected from the group consisting of polyvinylidene fluoride and a piezoelectric co-polymer material.

3. The sensor of claim 1 wherein said first and second sensing portions comprise end portions of a common piece of piezoelectric material.

4. The sensor of claim 3 further comprising:

said common piece of piezoelectric material having a continuously metallized outer surface and an inner surface metallized only at the end portions forming said first and second sensing portions.

5. The sensor of claim 1 further comprising:

first and second layers of a compliant, substantially incompressible material;

said first layer being positioned adjacent an inner surface of said first piezoelectric sensing portion; and said second layer being positioned adjacent an inner surface of said second piezoelectric sensing portion.

6. The sensor of claim 5 further comprising:

a neutral plane inducer positioned between said first and second layers.

7. The sensor of claim 6 wherein said neutral plane inducer is formed by a thin metal sheet.

8. The sensor of claim 6 wherein said neutral plane inducer is formed by a thin plastic sheet.

9. The sensor of claim 6 wherein said neutral plane inducer comprises a series of spaced apart narrow strips that traverse a narrow dimension of each of said first and second layers.

10. The sensor of claim 6 wherein said neutral plane inducer is formed by a layer of an adhesive material used to bond said first and second layers together.

11. The sensor of claim 6 wherein said first and second sensing portions have a tensile stiffness, said first and second layers have a tensile stiffness and said neutral plane inducer has a tensile stiffness several times larger than the tensile stiffness of said first and second layers and the tensile stiffness of said first and second sensing portions.

12. The sensor of claim 1 further comprising:

an electric connector along an edge of said sensor; and shield means placed over said connector for minimizing the generation of any interfering signals due to extraneous electromagnetic fields.

13. The sensor of claim 12 further comprising:

said connector having a central pin and two outer pins;

said outer pins each being connected to positive surfaces of said first and second sensing portions; and said central pin being electrically connected to at least one negative surface of said first and second sensing portions.

14. The sensor of claim 12 further comprising:

said connector having a central pin and two outer pins;

said outer pins each being connected to negative surfaces of said first and second sensing portions; and said central pin being electrically connected to at least one positive surface of said first and second sensing portions.

15. The sensor of claim 12 further comprising:

said shield means being formed by an insulating layer placed over said connector and a coating of at least one of a conductive ink, a conductive paint and metal foil over an inner surface of said insulating layer; and said coating being in electrical contact with an outer surface of said first and second sensing portions.

16. The sensor of claim 12 further comprising:

said shield means being formed by a metal layer about said first and second piezoelectric sensing portions.

17. The sensor of claim 1 further comprising a layer of an adherent material affixed to a surface of at least one of said first and second piezoelectric sensing portions, said adherent material layer adapted for maintaining intimate contact between said skin and said pad so that said pad flexes with said skin.

18. The sensor of claim 17 wherein said adherent layer material layer covers an area at least as large as the area of said surface of said sensor.

19. An acoustic sensor which comprises:

a strip of piezoelectric material having a metallized outer surface and a partially metallized inner surface;

said strip of piezoelectric material being folded so that a first end portion overlaps a second end portion;

said partially metallized inner surface including a first metal layer overlaying an inner surface of said first end portion and a second metal layer overlaying an inner surface of said second end portion;

said first and second end portions being spaced apart by a first layer formed from an insulating material, a neutral plane inducer, and a second layer formed from an insulating material;

said first insulating layer being positioned adjacent said inner surface of said first end portion and said second insulating layer being positioned adjacent said inner surface of said second end portion; and said neutral plane inducer being positioned intermediate said first and second insulating layers.

20. The sensor of claim 19 further comprising:

an electrical connector positioned along an edge of said sensor;

said connector having a first conductor electrically connected to said first metal layer, a second conductor electrically connected to said second metal layer, and a third conductor electrically connected to said metallized outer surface.

21. The sensor of claim 20 further comprising:

means for shielding said connector from interfering signals due to extraneous electromagnetic fields.

22. The sensor of claim 21 wherein said shielding means includes a layer of a conductive material overlaying a layer of an insulating material.

23. The sensor of claim 19 further comprising:

a layer of adherent material for maintaining intimate contact between the sensor and skin tissue of a patient.

24. The sensor of claim 23 wherein said sensor with said adherent material layer has a mechanical impedance which is adjusted in accordance with the mechanical impedance of a patient's body skin tissue and conforms to the contour of said patient's skin.

25. The sensor of claim 23 further comprising:

bib means for preventing said adherent material from contaminating said sensor having an electrical connector affixed thereto and a mating cable connector attached to said electrical connector.

26. The sensor of claim 19 further comprising a moisture barrier positioned adjacent a lower surface of said sensor.

* * * * *